(12) United States Patent
Voellmicke

(10) Patent No.: US 9,265,621 B2
(45) Date of Patent: Feb. 23, 2016

(54) COMPOSITE VERTEBRAL SPACERS AND INSTRUMENT

(71) Applicant: Medos International Sarl, Le Locle (CH)

(72) Inventor: John C. Voellmicke, Franklin, MA (US)

(73) Assignee: Medos International Sarl, Le Lode (CH)

( * ) Notice: Subject to any disclaimer, the term of this patent is extended or adjusted under 35 U.S.C. 154(b) by 0 days.

(21) Appl. No.: 14/698,179

(22) Filed: Apr. 28, 2015

(65) Prior Publication Data

US 2015/0230937 A1 Aug. 20, 2015

Related U.S. Application Data

(62) Division of application No. 11/615,077, filed on Dec. 22, 2006, now Pat. No. 9,039,768.

(51) Int. Cl.
*A61F 2/44* (2006.01)

(52) U.S. Cl.
CPC ............... *A61F 2/4455* (2013.01); *A61F 2/442* (2013.01)

(58) Field of Classification Search
CPC .................................................... A61F 2/4455
See application file for complete search history.

(56) References Cited

U.S. PATENT DOCUMENTS

| | | | |
|---|---|---|---|
| 4,743,256 A | 5/1988 | Brantigan | |
| 5,397,364 A | 3/1995 | Kozak et al. | |
| 5,609,636 A | 3/1997 | Kohrs et al. | |
| 5,620,458 A | 4/1997 | Green | |
| 5,716,415 A | 2/1998 | Steffee | |
| 6,039,761 A | 3/2000 | Li et al. | |
| 6,117,174 A | 9/2000 | Nolan | |
| 6,159,244 A | 12/2000 | Suddaby | |
| 6,179,875 B1 | 1/2001 | Von Strempel | |
| 6,193,757 B1 | 2/2001 | Foley et al. | |
| 6,395,031 B1 | 5/2002 | Foley et al. | |
| 6,413,278 B1 | 7/2002 | Marchosky | |
| 6,761,738 B1 | 7/2004 | Boyd | |
| 6,824,565 B2 | 11/2004 | Muhanna | |
| 6,833,006 B2 | 12/2004 | Foley et al. | |
| 6,835,208 B2 | 12/2004 | Marchosky | |
| 6,974,480 B2 | 12/2005 | Messerli | |
| 7,056,341 B2 | 6/2006 | Crozet | |
| 7,655,042 B2 | 2/2010 | Foley et al. | |
| 7,846,206 B2 | 12/2010 | Leonard et al. | |
| 7,871,441 B2 | 1/2011 | Eckman | |
| 7,993,403 B2 | 8/2011 | Foley et al. | |
| 2001/0031968 A1 | 10/2001 | Dorchak et al. | |
| 2002/0138146 A1 | 9/2002 | Jackson | |
| 2002/0151976 A1 | 10/2002 | Foley et al. | |
| 2003/0004576 A1 | 1/2003 | Thalgott | |
| 2003/0083748 A1 | 5/2003 | Lee et al. | |
| 2004/0106996 A1 | 6/2004 | Liu | |
| 2005/0113920 A1 * | 5/2005 | Foley et al. | 623/17.11 |
| 2005/0209696 A1 | 9/2005 | Lin | |
| 2006/0025860 A1 | 2/2006 | Li | |

(Continued)

OTHER PUBLICATIONS

European Examination Report dated Mar. 19, 2014 for EP07855287.4.

(Continued)

*Primary Examiner* — Ellen C Hammond
(74) *Attorney, Agent, or Firm* — Baker & Hostetler LLP

(57) ABSTRACT

An intervertebral fusion cage that is adapted to contain an inserter within its inner volume during insertion of the cage.

23 Claims, 20 Drawing Sheets

(56) References Cited

U.S. PATENT DOCUMENTS

2006/0229729 A1 10/2006 Gordon
2009/0198339 A1 8/2009 Kleiner

OTHER PUBLICATIONS

Examination Report dated Mar. 22, 2012 for AU2007336858.
Search Report dated Jan. 20, 2012 for EP07855287.

* cited by examiner

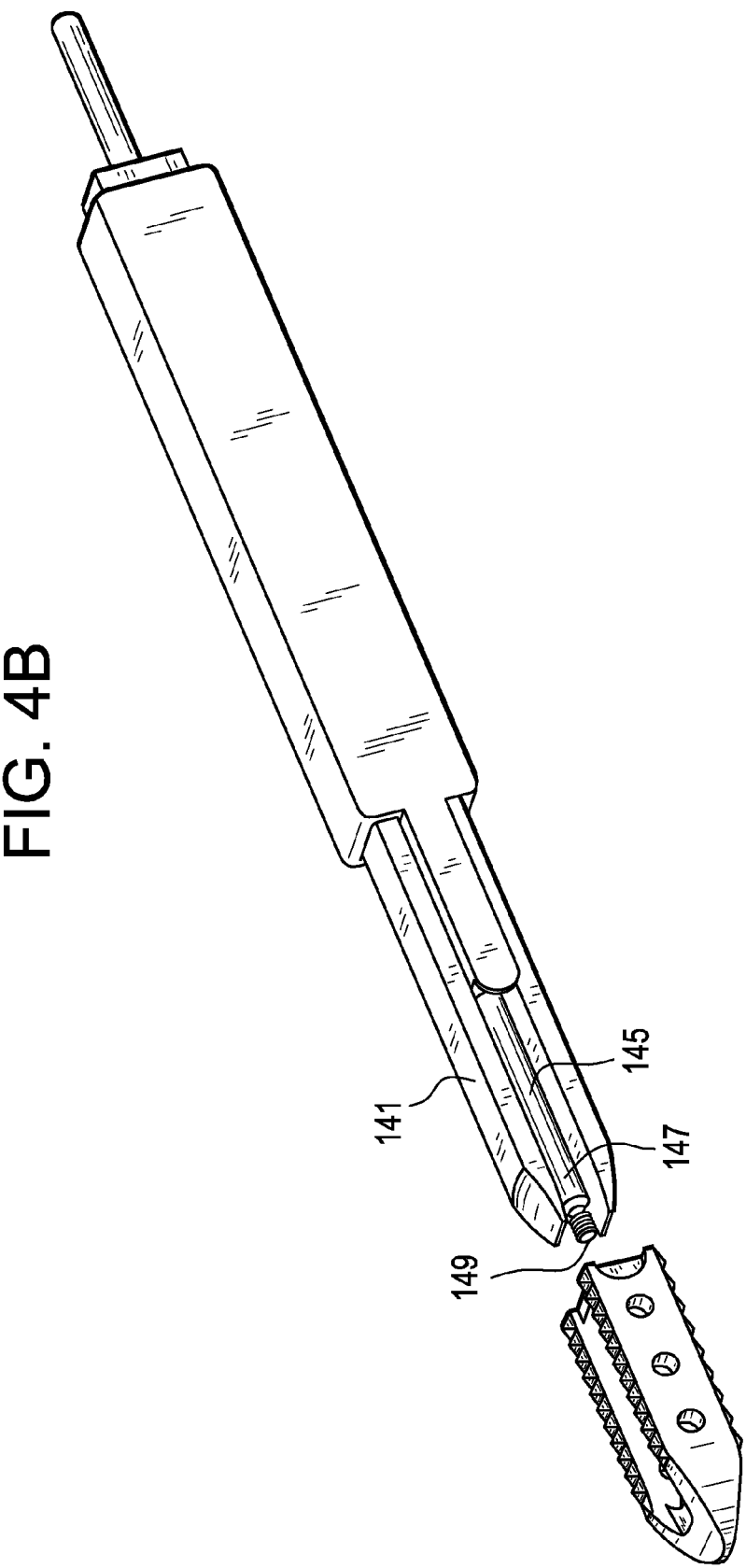

COMPOSITE VERTEBRAL SPACERS AND INSTRUMENT

CROSS-REFERENCE TO RELATED APPLICATIONS

This application is a divisional of U.S. patent application Ser. No. 11/615,077, filed Dec. 22, 2006, which is incorporated herein by reference.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). These cytokines and MMPs help regulate the metabolism of the nucleus pulposus cells.

In some instances of degenerative disc disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of proinflammatory cytokines and/or MMPs that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing their water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices".

Designs of intervertebral fusion devices are generally either box-like (i.e., Smith-Robinson style) or threaded cylinders (i.e., Cloward style). Smith-Robinson style implants have the advantage of better contact area to the endplates, but rely on a coarse surface texture or teeth to prevent migration once implanted. Insertion then requires over distraction of the disc space to slide the implant in or to provide a smoother implant, which can migrate post-op.

One such box-like design is the Brantigan cage. U.S. Pat. No. 4,743,256 ("Brantigan") discloses an improved surgical method for eliminating spinal back pain caused by ruptured or degenerated vertebral discs by spanning the disc space between adjacent vertebrae with rigid fusion devices, or "cages", having surfaces facilitating bone ingrowth and bottomed on prepared sites of the vertebrae to integrate the implant with the vertebrae and to provide a permanent weight supporting strut maintaining the disc space.

One commericial box-like design is the injection-molded carbon fiber reinforced PEEK (CFRP) cage made by DePuy Spine. However, these cages are difficult to insert because of the interference fit produced between the textured, toothed upper and lower surfaces of the implant and the bony endplates. Simply, the presence of teeth extending from the upper and lower surfaces of the cage make its insertion difficult. In addition, the reinforced PEEK material is brittle and so is prone to breakage when applying impact or torque loads to the implant to overcome tooth-induced resistance during insertion and final positioning of the implant.

Current interbody devices are made from single materials (e.g., machined titanium, or molded and/or machined PEEK). Titanium has the disadvantage of being radiopaque (which can interfere with fusion assessment on x-ray) while also having a high modulus of elasticity (which can stress shield the bone graft). Injection molded CFRP is very brittle and prone to fracture during insertion. Unfilled PEEK is much less brittle but also weaker than carbon-filled PEEK, requiring thicker-walled designs (diminishing space for bone graft). Both PEEK and carbon-filled PEEK are radiolucent.

U.S. Pat. No. 6,761,738 ("Boyd") discloses a modular intervertebral spacer formed from assembled bone-derived components. In particular, Boyd discloses an assembly of vertical planks with cylindrical cross pins. However, Boyd does not disclose the use of non-allograft materials of construction, any companion instrumentation for insertion of the device, nor a method of placing the device first into the disc space and then filling it with a biologic material Allograft bone is very brittle, and so it is difficult to securely join such pieces together.

U.S. Pat. No. 6,413,278 and U.S. Pat. No. 6,835,208 ("Marchosky") disclose an I-beam shaped implant whose top and bottom surface flex under anatomic loads. There is no interior space to this implant, and Marchosky teaches that two such implants need be implanted in a single disc space. Although a syringe for injecting bone graft around the implant is disclosed, a mating inserter instrument for placing the implant is not disclosed.

U.S. Pat. No. 6,824,565 ("Muhana") discloses implant and instrument designs wherein some of the implant embodiments have planked designs and a mating inserter instrument. However, the disclosed inserter wraps around the exterior of the implant and partially into grooves on the implant. The disclosed implant is derived from bone and is not hollow. The insertion technique disclosed by Muhana requires a cutting tool to prepare a channel for the implant.

US2005/0209696 (Lin) discloses an intervertebral implant system for intervertebral implantation, wherein the system includes a frame having a peripheral wall defining a space therein, and a settable material introducible into the space of the frame. The settable material is a biocompatible load bearing material including and not limited to bone, composites, polymers of bone growth material, collagen, and insoluble collagen derivatives. The settable material is injectable into the space defined by the frame. The settable material may have an initial fluid condition wherein the fluid settable material cures to a hardened condition. Lin further includes the steps of accessing the disc space between adjacent intervertebral discs; removing disc material from the disc space; distracting the disc space; preparing the end plates of the adjacent intervertebral discs; inserting the peripheral wall of the frame into the disc space between the adjacent intervertebral discs; and injecting settable material into the space defines by the peripheral wall of the frame and between the adjacent intervertebral discs. Lin teaches that the method may further include the step of connecting each free end of the peripheral wall to one another. Lin teaches that the method further includes the steps of inserting a plurality of frames into the disc space between the adjacent intervertebral discs, wherein each frame defines a space; and injecting settable material into at least one of the spaces defined by the frames.

In summary, the insertion of both smooth and toothed intervertebral cages has proven to be problematic. Whereas toothed cages are difficult to insert, cages with smooth upper and lower surfaces have demonstrated undesirable migration.

SUMMARY OF THE INVENTION

With the availability of an injectable bone graft material, it is appreciated by the present inventor that a fusion cage can now be placed into the disc space in an empty condition (i.e., without pre-packed morselized bone graft) and then filled with injectable bone graft in a minimally invasive manner. This procedure now allows the surgeon to fill the interior of the cage with an insertion instrument during cage insertion in order to create a more secure mating condition with the implant without adding to the overall size of the implant.

Moreover, under such conditions, because the inserter can now occupy space along the length of the cage, it can also be used to ease entry of the cage into the disc space. In particular, the inserter can be provided with a height that is just slightly taller than the cage and with smooth upper and lower surfaces. When the smooth surfaces of the inserter extend to be just proud of the cage teeth, they help distract the disc space during insertion and greatly reduce insertion-generated friction to improve the ease with which the cage is inserted. When the inserter is removed after the cage has been inserted into the disc space, the adjacent boney endplates of the patient will collapse upon the cage, and the aggressive teeth of the cage will engage the bone and effectively prevent migration of the implant. Therefore, the cage and inserter of the present invention overcome the prior art problems associated with conventional toothed and smooth cages by not only allowing for easy insertion, but also providing a firm, migration-resistant grip.

Therefore, this invention improves the ease of insertion and placement of an intervertebral spacer, eliminates damage to the spacer during insertion and placement, resists implant migration, and maintains maximum volume for bone graft within the spacer and surrounding disc space.

Therefore, in accordance with the present invention, there is provided an intervertebral fusion cage, comprising:
a) a leading end having a right and left ends, a front surface and a back surface, the back surface being adapted for reception of a rod,
b) first and second support members extending backwards from the right and left ends and terminating in a respective back surface, each member having an upper and lower surface adapted for bearing against and gripping adjacent vertebral bodies,
c) an open trailing end formed by the back surfaces of the support members.

Also in accordance with the present invention, there is provided a method of inserting a fusion cage, comprising the steps of:
a) providing an intervertebral fusion cage having an interior space,
b) providing an inserter rod having a distal end and an intermediate portion,
c) coupling a distal end of a rod to the cage so that the intermediate portion of the cage occupies interior space of the cage,
d) inserting the cage into an intervertebral space,
e) withdrawing the rod from the cage, and
f) adding a flowable graft material to the interior space of the cage.

DESCRIPTION OF THE FIGURES

FIGS. 4B-4C are exploded perspective views of a second cage-inserter assembly of the present invention.

DETAILED DESCRIPTION OF THE INVENTION

Figure 1A:
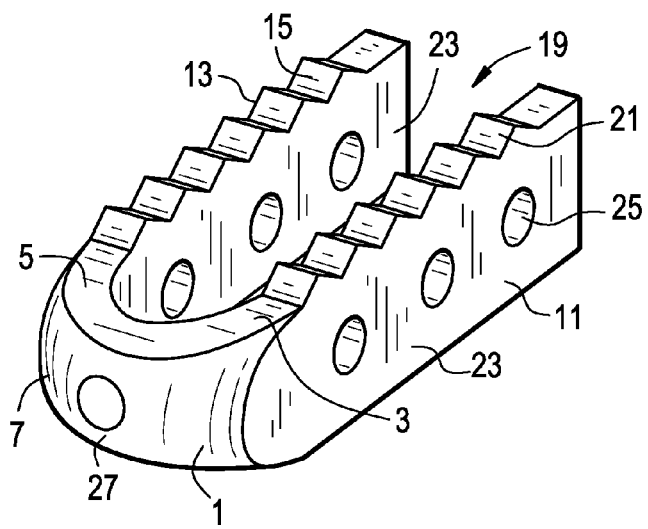
FIGS. 1A-1D are different views of a first intervertebral cage of the present invention.
Figure 1B:
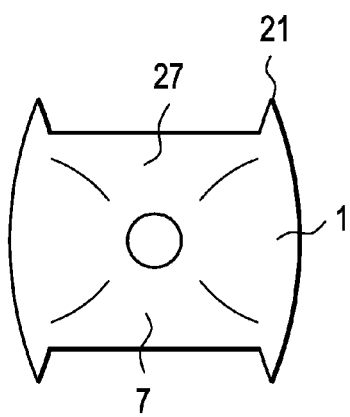
Figure 1C:
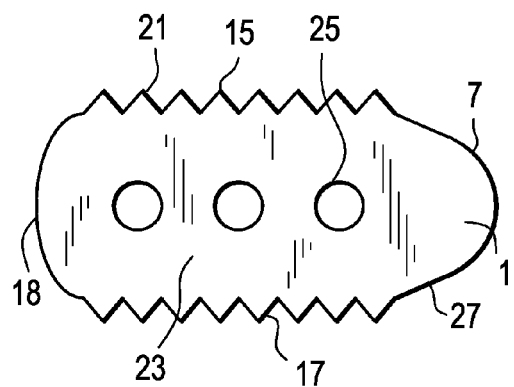

The present invention relates to a spinal interbody spacer that is easy to insert, fracture resistant, migration resistant, and fillable with a flowable biologic material after insertion.

Now referring to FIGS. 1A-1D, there is provided an intervertebral fusion cage, comprising:
a) a leading end 1 having a right 3 and left 5 ends, a front surface 7 and a back surface 9, the back surface being adapted for reception of a rod,
b) first 11 and second 13 support members extending backwards from the right and left ends, each member having an upper 15 and lower 17 surface adapted for bearing against and gripping adjacent vertebral bodies and a proximal surface 18, and
c) an open trailing end 19 formed between the back surfaces of the support members.

Upon each of the upper and lower surfaces of the cage, there is provided a plurality of teeth 21. When the cage is inserted and the inserter is removed, these teeth bite into the adjacent vertebral bodies and thereby resist migration of the cage.

Each of the support members further comprises a side surface 23 extending between its upper and lower surfaces, each side surface having at least one transverse hole 25 therethrough. The transverse hole allows bone growth therethrough, thereby further securing the cage within the intervertebral space.

In some embodiments, the front surface of the leading end of the cage is tapered. This tapered nose 27 can distract the disc space during its insertion into the disc space, thereby providing for ease of insertion.

Figure 1D:
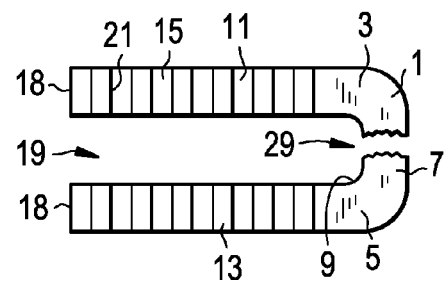
Figure 2A:
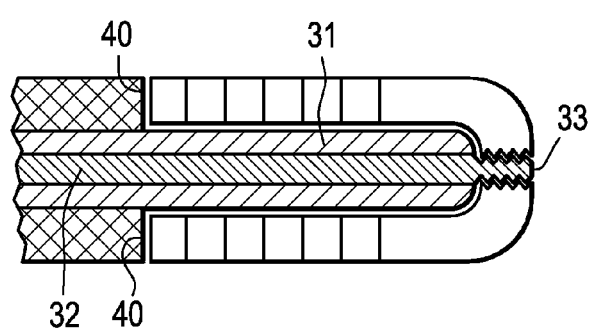
FIGS. 2A-2B are cross sections of a cage of the present invention having an inserter housed therewithin.

Also shown in FIG. 1D, the back surface of the leading end of the cage forms a recess 29 for reception of a rod. In FIGS. 1A-1D, the recess is a throughhole. The throughhole may be threaded. As shown in FIG. 2A, coupling of the back surface of the leading end of the cage with the threaded distal end 33 of the rod 32 allows the surgeon to use the rod as an inserter and insert the cage in a minimally invasive manner. In some embodiments (and as shown in FIGS. 1A-1D), the back surface of the leading end of the cage forms a concave recess for reception of a rod. The concave recess is a simple design choice that provides the needed coupling with the rod and allows the rod to have a substantially rectangular cross-section.

In other embodiments, the back surface of the leading end forms a threaded recess for threadable reception of a rod.

As shown, the ends of the leading end and the support members are integrally connected.

In preferred embodiments, the back surfaces of the support members of the cage are used as stabilizers whereby a forward force upon these back surfaces carefully counterbalances the backward force used to withdraw the rod from the cage. This forward force keeps the cage in the disc space during withdrawal of the rod. Preferably then, the back surfaces are configured to stably receive the laterally-spaced extensions that extend from the distal face of the cannula and provide the biasing forward force. In some embodiments thereof, the back surface of each support member has a concave recess providing such stability. However, in other embodiments, the back surface of each support member may be flat.

Figure 2B:
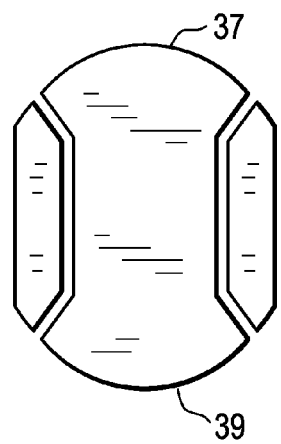
Figure 2C:
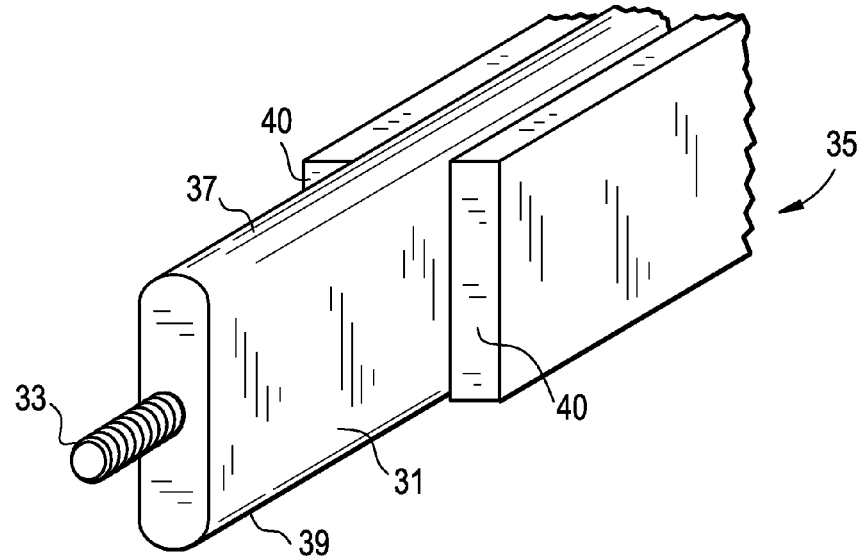
FIG. 2C is a perspective view of an inserter of the present invention.

In use, the "U" shaped implant of FIG. 1A is coupled with the metal inserter 35 of FIG. 2C so that the metal inserter occupies the interior space of the cage, as shown in FIGS. 2A-2B. Since the inserter is slightly taller than the cage, the smooth upper 37 and lower 39 surfaces of the metal inserter are just proud of the level of the tooth peaks of the cage. These smooth upper and lower surfaces of the metal inserter should therefore be the only part of the assembly that contacts the adjacent vertebral bodies. Therefore, when the implant is inserted, the entire insertion load is borne by the metallic inserter, thereby reducing the chances of damaging the implant. Moreover, since the contact surfaces are smooth, the insertion will be carried out under low friction, thereby increasing the ease of insertion. The cage is then held in place by the extension components 40 of the inserter while the rod component 32 (which is slidably received in annulus 31) is uncoupled from the cage and retracted out of the annulus 31. Annulus 31 is then retracted to a position just outside out of the cage, thereby allowing the adjacent bone to contact the cage. The empty cage is then filled with flowable bone graft by introducing bone graft through the annulus 31.

Therefore, in accordance with the present invention, there is provided an assembly comprising:
a) an intervertebral fusion cage having an interior space, and
b) a rod adapted to insert the cage into an intervertebral space, the rod having a distal end and an intermediate portion,
wherein the distal end of the rod is connected to the cage, and wherein the intermediate portion of the rod is housed within the interior space of the cage.

Also in accordance with the present invention, there is provided a method of inserting a fusion cage, comprising the steps of:
a) providing an intervertebral fusion cage having a leading end having a back surface and a trailing end,
b) coupling a distal end of an inserter having a slidable rod therein to the back surface of the leading end of the cage,
c) inserting the cage into an intervertebral space,
d) withdrawing the rod from the cage.

Figure 3A:
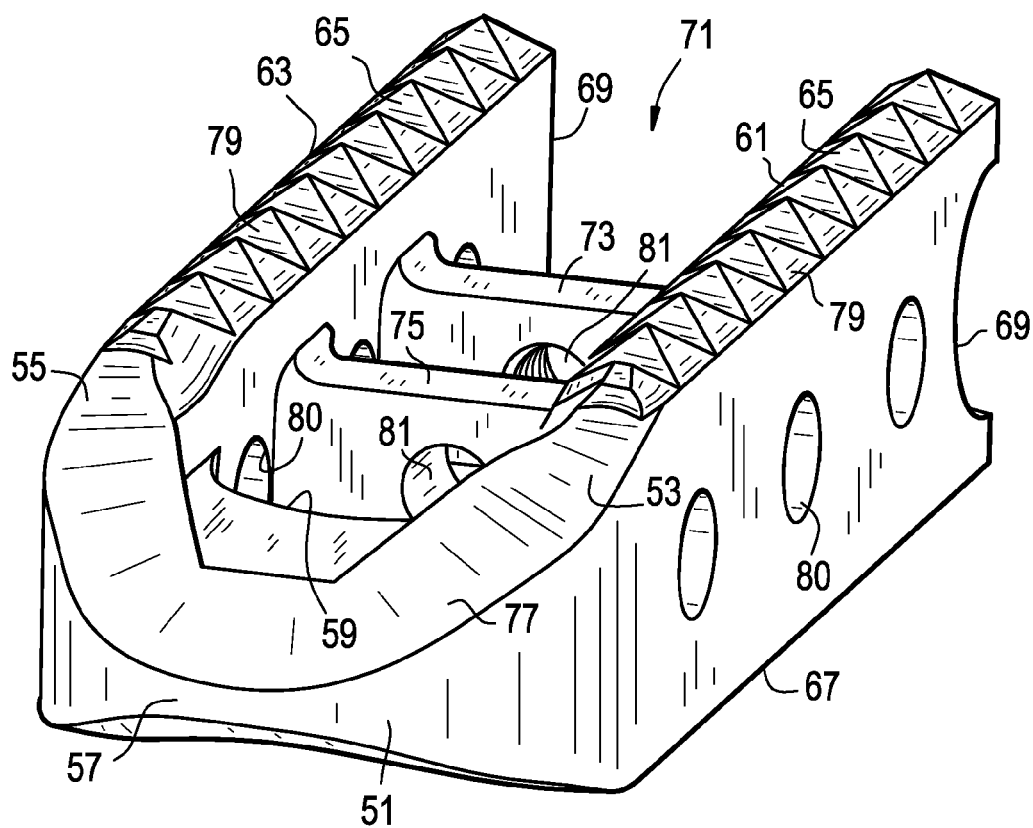
FIG. 3A is a perspective view of a second embodiment of a cage of the present invention.

Now referring to FIG. 3A, in a first preferred embodiment, there is provided an intervertebral fusion cage, comprising:
a) a leading end 51 having a right 53 and left 55 ends, a front surface 57 and a back surface 59, the back surface being adapted for reception of a rod,
b) first 61 and second 63 support members extending backwards from the right and left ends, each member having an upper 65 and lower 67 surface adapted for bearing against and gripping adjacent vertebral bodies, and proximal end surfaces 69,
c) an open trailing end 71 formed between the proximal end surfaces, and
d) a first 73 and second 75 elongate cross-members, each extending from the first support member to the second support member.

Preferably, as shown, the leading end has an arcuate shape. Also preferably, the leading end has a beveled nose 77 defined by converging upper and lower surfaces. This beveled nose facilitates cage insertion.

Preferably, the upper and lower surfaces of the support members are adapted for gripping the opposing vertebral endplates. Preferably, these surfaces contain outwardly extending teeth 79 that provide stability to the cage.

Preferably, each support member has a throughhole 80 extending therethrough and each cross-member has a throughhole 81 extending therethrough. The cross members provide for substantial containment of the injectable bone graft paste and add stiffness to the construct. These holes are adapted for encouraging bone growth therethrough.

As shown, the cage preferably has a substantially rectangular cross-section.

In this embodiment, an inserter rod can anchor into the back surface of the leading end of the cage.

Therefore, in accordance with the present invention, there is provided an intervertebral fusion cage, comprising:
a) a leading end having a right and left ends, a front surface and a back surface,
b) first and second support members extending backwards from the right and left ends and terminating in a respective back surface, each member having an upper and lower surface adapted for bearing against and gripping adjacent vertebral bodies,
c) an open trailing end formed by the back surfaces of the support members, and
d) a strut connecting the first and second support members, the strut being located between the leading end and the open trailing end of the cage, the strut having a back surface being adapted for reception of an inserter rod.

Figure 3B:
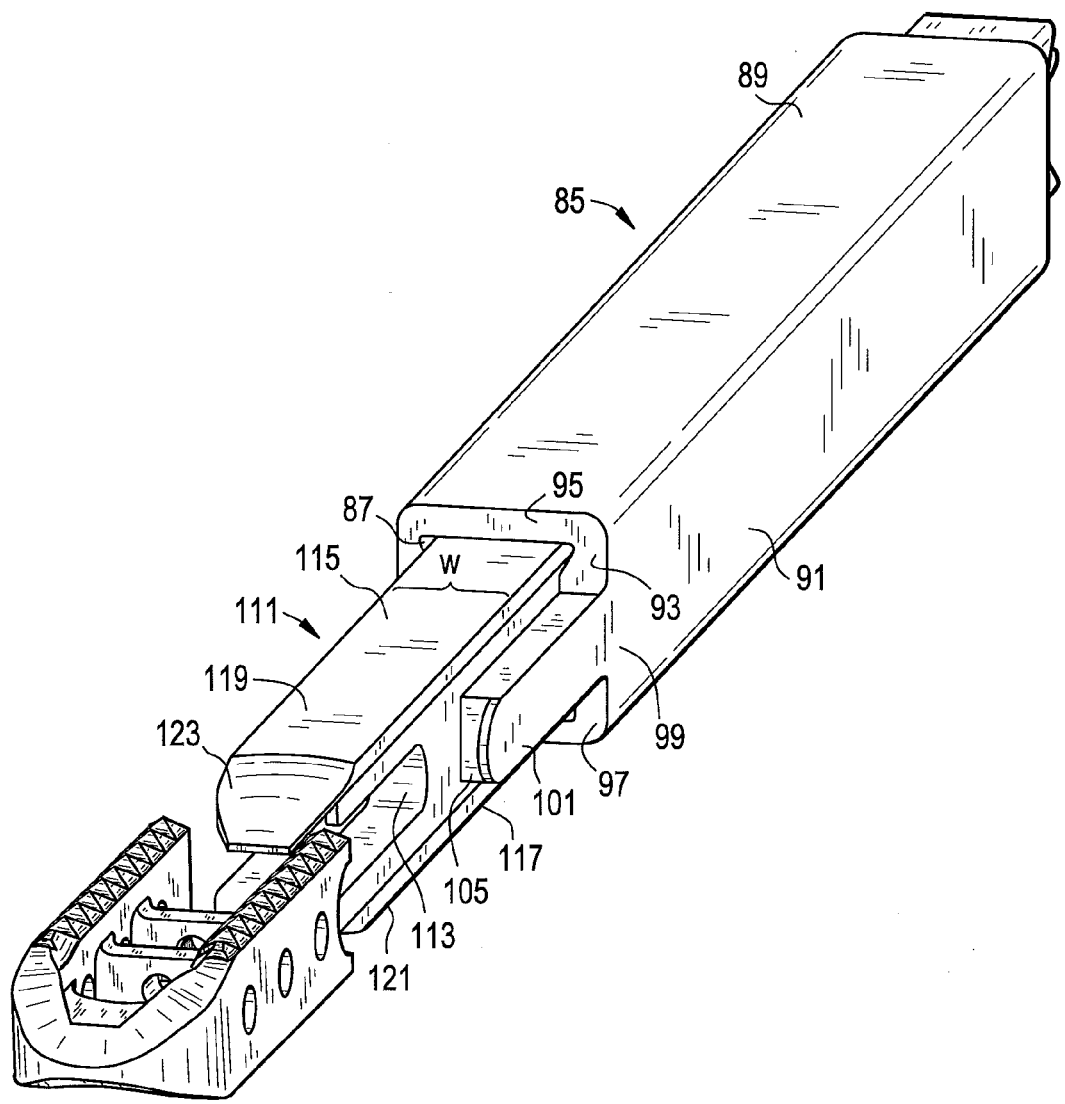
FIGS. 3B-3C are exploded perspective views of a first cage-inserter assembly of the present invention.
Figure 3C:
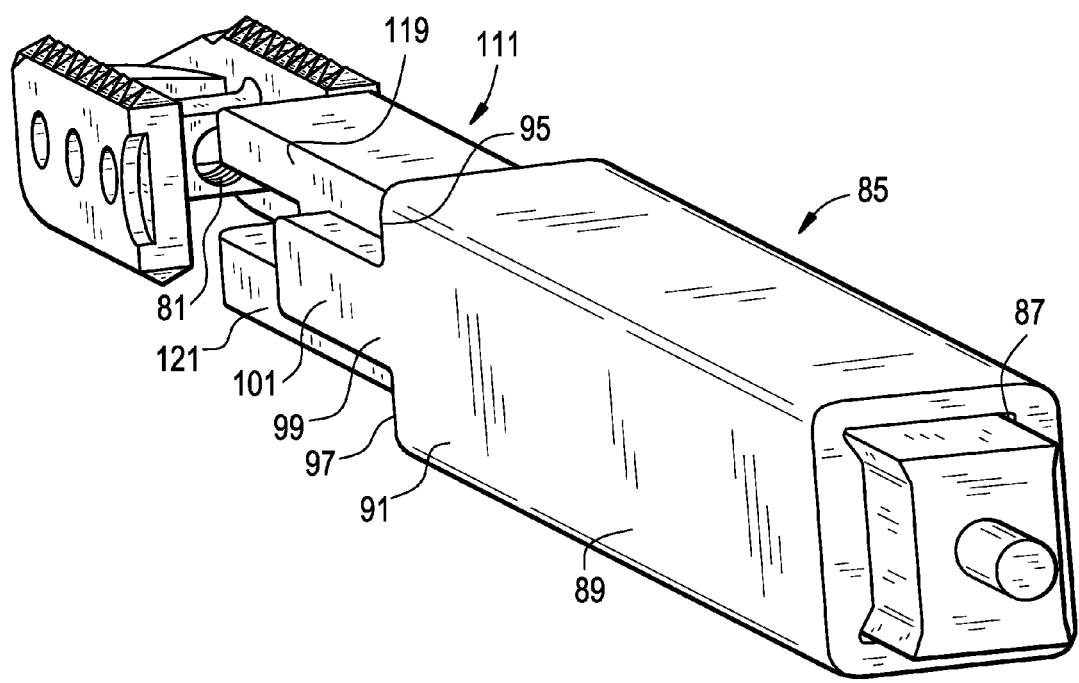

FIGS. 3B and 3C are exploded versions of the cage and inserter assembly, as viewed from the distal and proximal perspectives.

The cage is the cage shown in FIG. 3A. As seen on FIG. 3C, the back surface of the leading end of the cage includes a throughhole 81 adapted for reception of a rod. These holes allow the inserter rod to pass through to the leading end of the cage.

The inserter of FIGS. 3B and 3C includes two components and comprises:
a) an outer annulus 85 having a longitudinal throughhole 87, a proximal end portion 89 and a distal end portion 91, the distal end portion including a distal end surface 93 having an upper surface 95, a lower surface 97 and a pair of lateral surfaces 99, each lateral surface having first and second arms 101 extending distally therefrom, each arm having a distal end surface 105 respectively adapted for bearing against a proximal end surface of the cage,
b) an inner rod 111 slidable within the longitudinal throughhole of the annulus and having a distal end surface 113, upper 115 and lower 117 surfaces, and upper 119 and lower 121 arms extending from the distal end surface, each arm including a beveled distal end 123 adapted to be coplanar with the beveled nose of the cage, each arm having a width W adapted for slidable reception between the support members of the cage.

Therefore, in accordance with the present invention, there is provided an apparatus for inserting a fusion cage having a leading end and a trailing end, comprising:
a) a cannula having a bore therethrough, a distal end face and at least two extensions extending distally from the distal end face, each extensions having a distal end adapted for bearing against the trailing end of the cage, and
b) a rod slidably received within the bore of the cannula, the rod having a distal end adapted for bearing against the leading end of the cage.

Figure 3D:
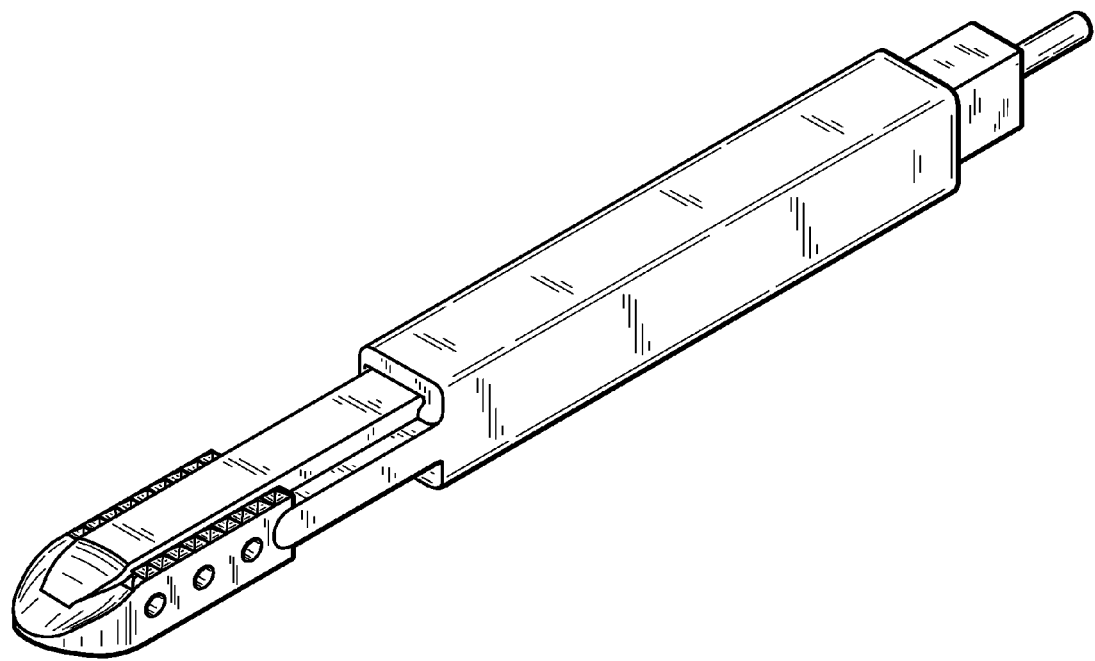
FIG. 3D is an assembled perspective view of the first cage-inserter assembly of the present invention.

Also in accordance with the present invention, there is provided an assembly comprising:
a) an intervertebral fusion cage having a leading end and a trailing end, and
b) an inserter comprising:
  i) a cannula having a bore therethrough, a distal end face and at least two extensions extending distally from the distal end face, each extension having a distal end bearing against the trailing end of the cage, and
  ii) a rod slidably received within the bore of the cannula, the rod having a distal end bearing against the leading end of the cage Lastly, FIG. 3D shows the assembled version of this cage and inserter assembly.

In use, the assembly of FIG. 3D is first constructed. In this assembled state, the arms of the inner rod extend over the cross-members of the cage so that its beveled nose is flush (here, coplanar) with the beveled nose of the cage. The arms of the outer annulus component of the inserter bear against the respective proximal end surfaces of the cage. Next, the distal end of the cage is delivered into the disc space, with the beveled nose of the cage providing distraction of the disc space. The assembly is then moved distally so that the entire cage is within the disc space. Next, the outer annulus of the inserter is held in place as the inner rod component is withdrawn. The bearing of the distal end surface of each arm of the inserter against the proximal end surfaces of the cage during inner rod withdrawal insures that the cage remains in place. Once the inner rod is completely withdrawn, the outer annulus is then moved proximally away from the cage and removed from the patient.

Figure 4A:
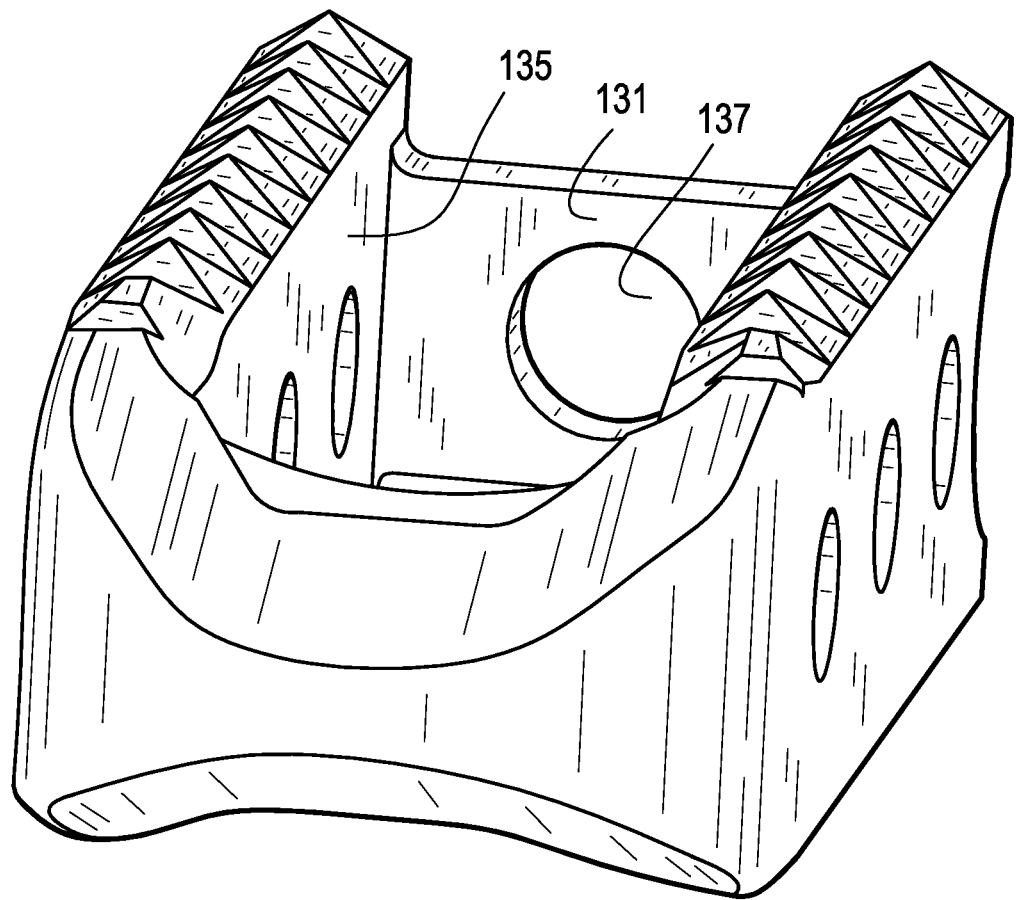
FIG. 4A is a perspective view of a third embodiment of a cage of the present invention.

Now referring to FIG. 4A, in a second preferred embodiment, there is provided an intervertebral fusion cage substantially similar to that of FIG. 3A, except that there is a single cross-member 131 connecting the supporting members and it is located in the proximal end portion 135 of the cage. In addition, the throughhole 137 of the cross-member is somewhat larger than that of FIG. 3A (and is adapted for reception of a threaded rod). In some embodiments, injectable graft material is delivered through this throughhole 137.

Figure 4C:
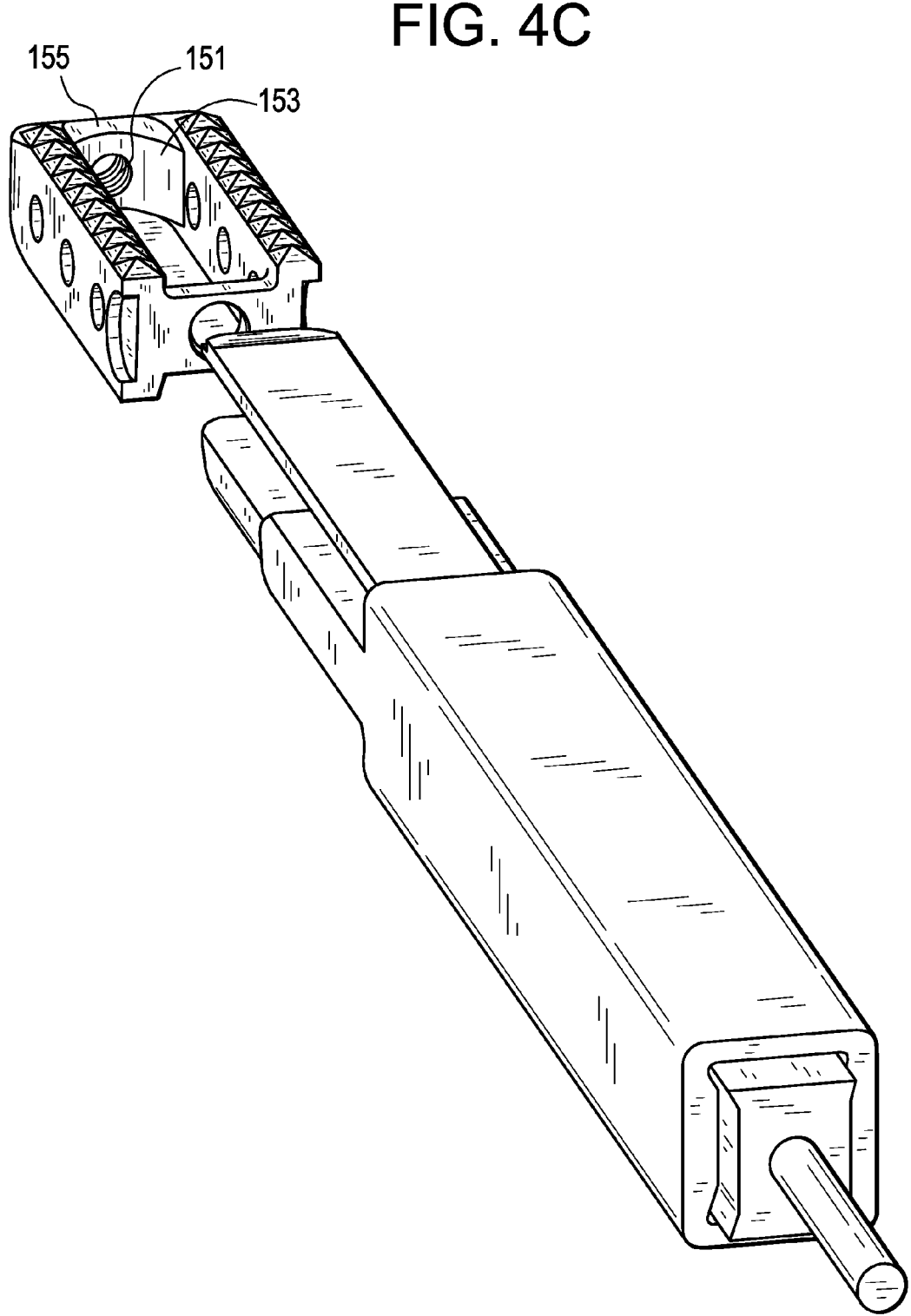

FIGS. 4B and 4C are exploded versions of the cage and inserter assembly, as viewed from the distal and proximal perspectives. The cage is the cage of FIG. 4A. The inserter assembly is substantially similar to that of FIGS. 3B and 3C, except that the inner rod 141 also has a longitudinal throughhole, and a threaded rod 145 is slidably received within the longitudinal throughhole of the inner rod. The distal end 147 of the threaded rod has a threadform 149 thereon that is adapted to mate with a threadform 149 within the hole 151 in the back surface 153 of the leading end 155 of the cage. The coupling of the threaded rod with the threaded hole on the back surface of the leading end of the cage provides stability for the cage during its insertion into the disc space.

Figure 4D:
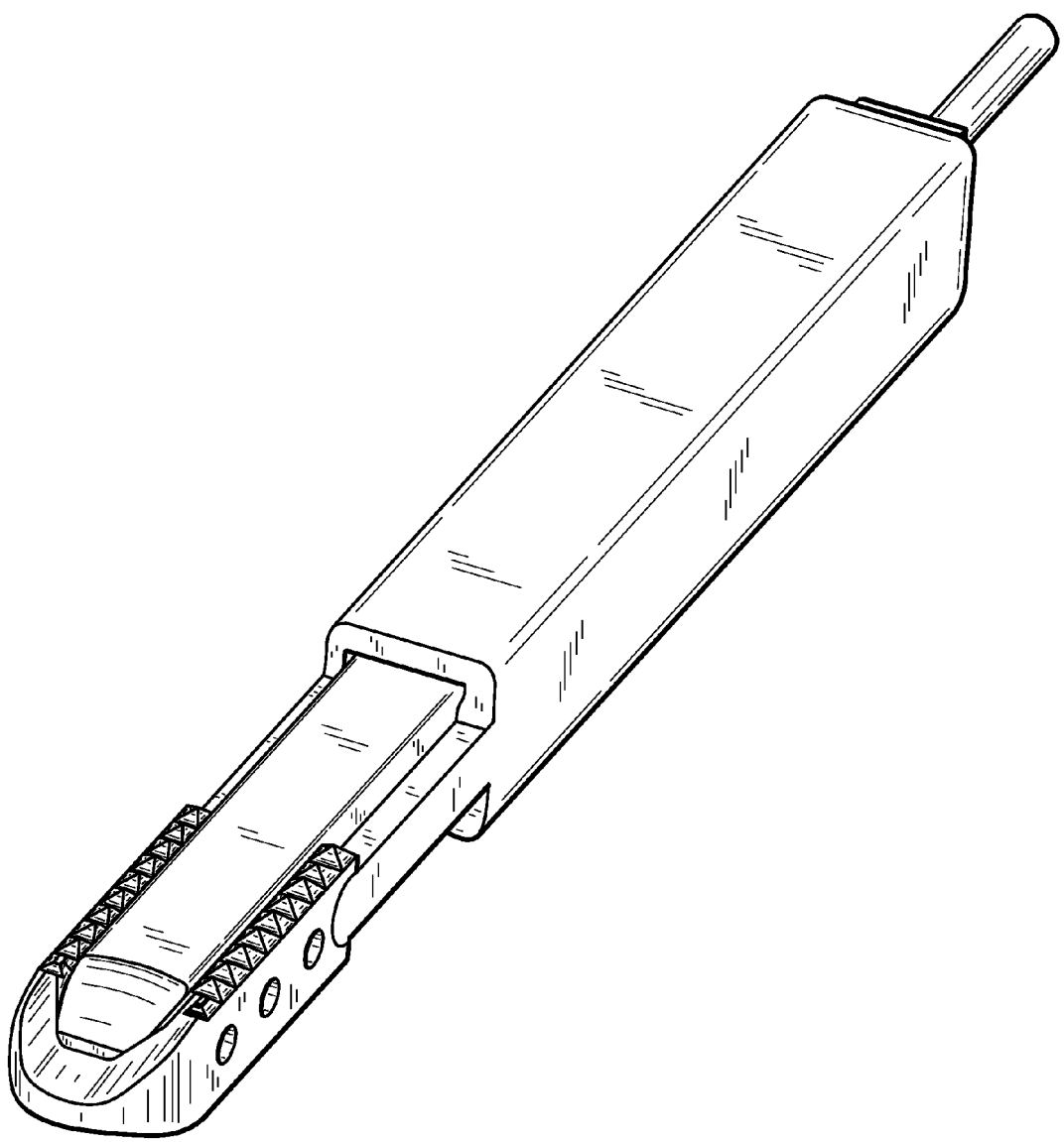
FIG. 4D is an assembled perspective view of the second cage-inserter assembly of the present invention.

The assembled version of FIGS. 4B and 4C is shown in 4D. Although not shown in FIG. 4D, the threaded distal end of the rod passes through the throughhole of the cross-member of the cage and is received in the threaded hole on the back surface of the leading end of the cage. The coupling of these threadforms provides stability to the cage during insertion. After the cage has been inserted, the threaded rod is disengaged from the threaded hole of the cage. Next, both the threaded rod and the inner rod are simultaneously removed from the disc space, as the outer annulus component of the inserter remains bearing against the proximal ends of the cage to insure that the cage remains in place. Lastly, the outer annulus is removed.

It has further been appreciated that if only the threaded inner rod is removed, then there exists a channel in the insertion instrument through which injectable bone graft material can be injected.

Figure 5A:
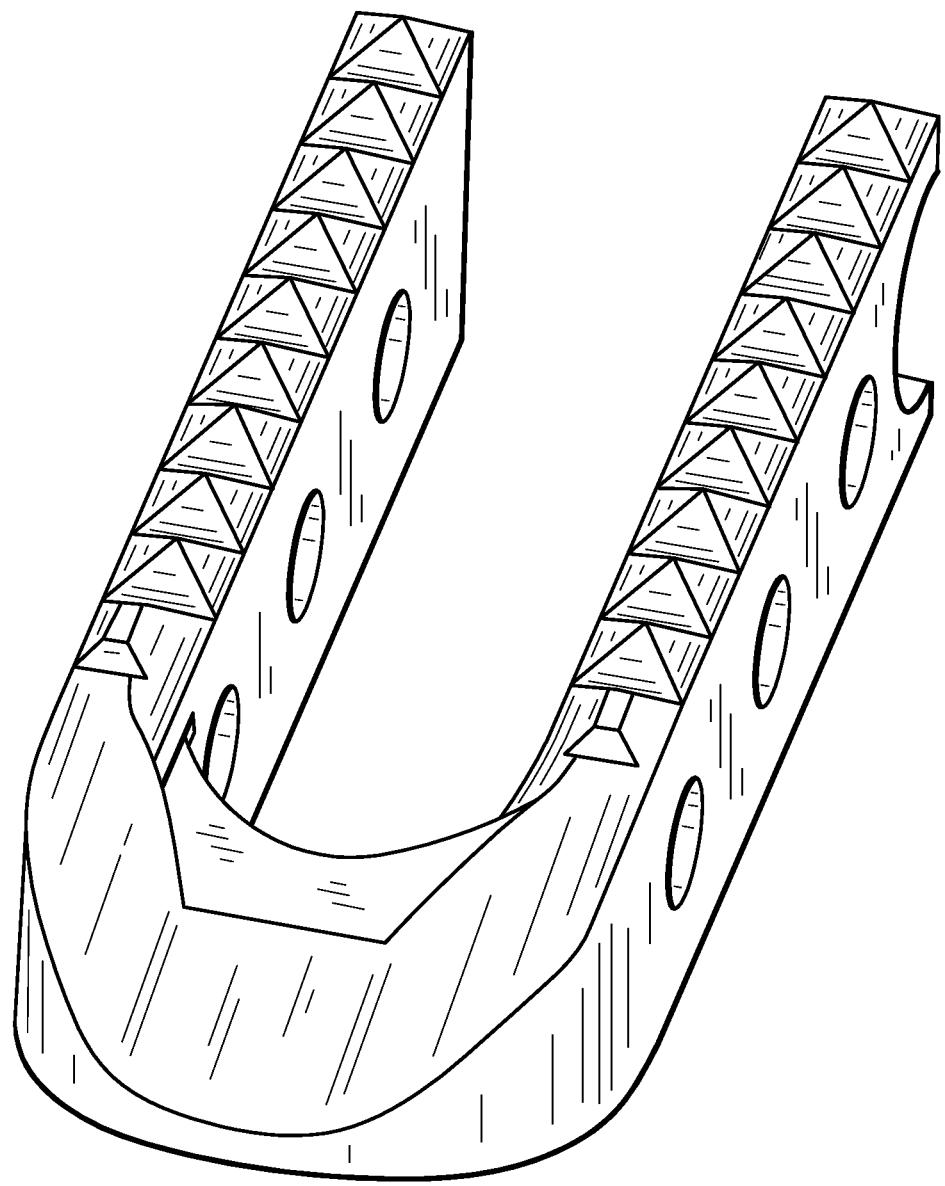
FIG. 5A is a perspective view of a fourth embodiment of a cage of the present invention.

Now referring to FIG. 5A, in a third preferred embodiment, there is provided an intervertebral fusion cage substantially similar to that of FIG. 4A, except that there is no cross-member.

Figure 5B:
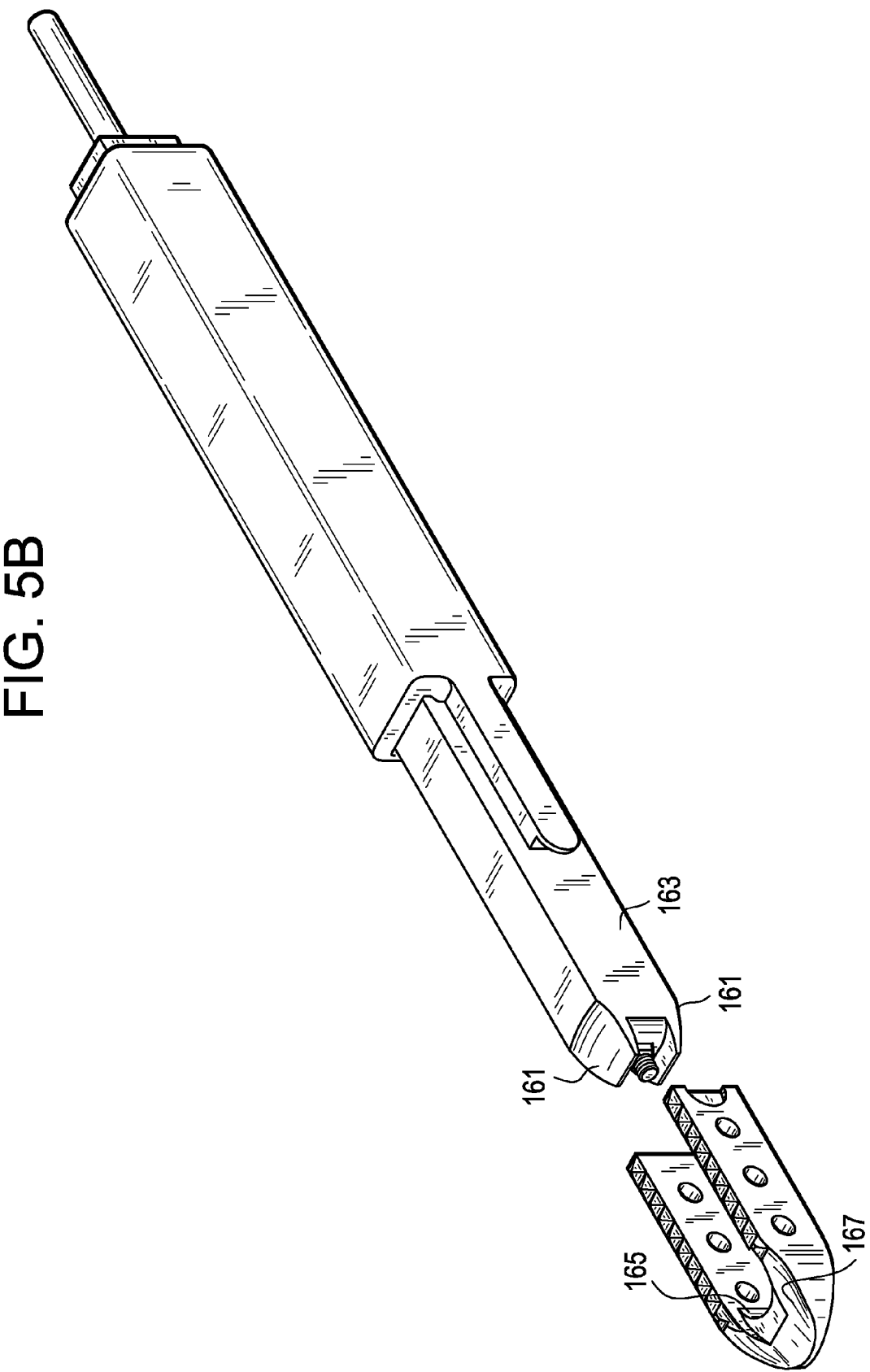
FIGS. 5B-5C are exploded perspective views of a third cage-inserter assembly of the present invention.
Figure 5C:
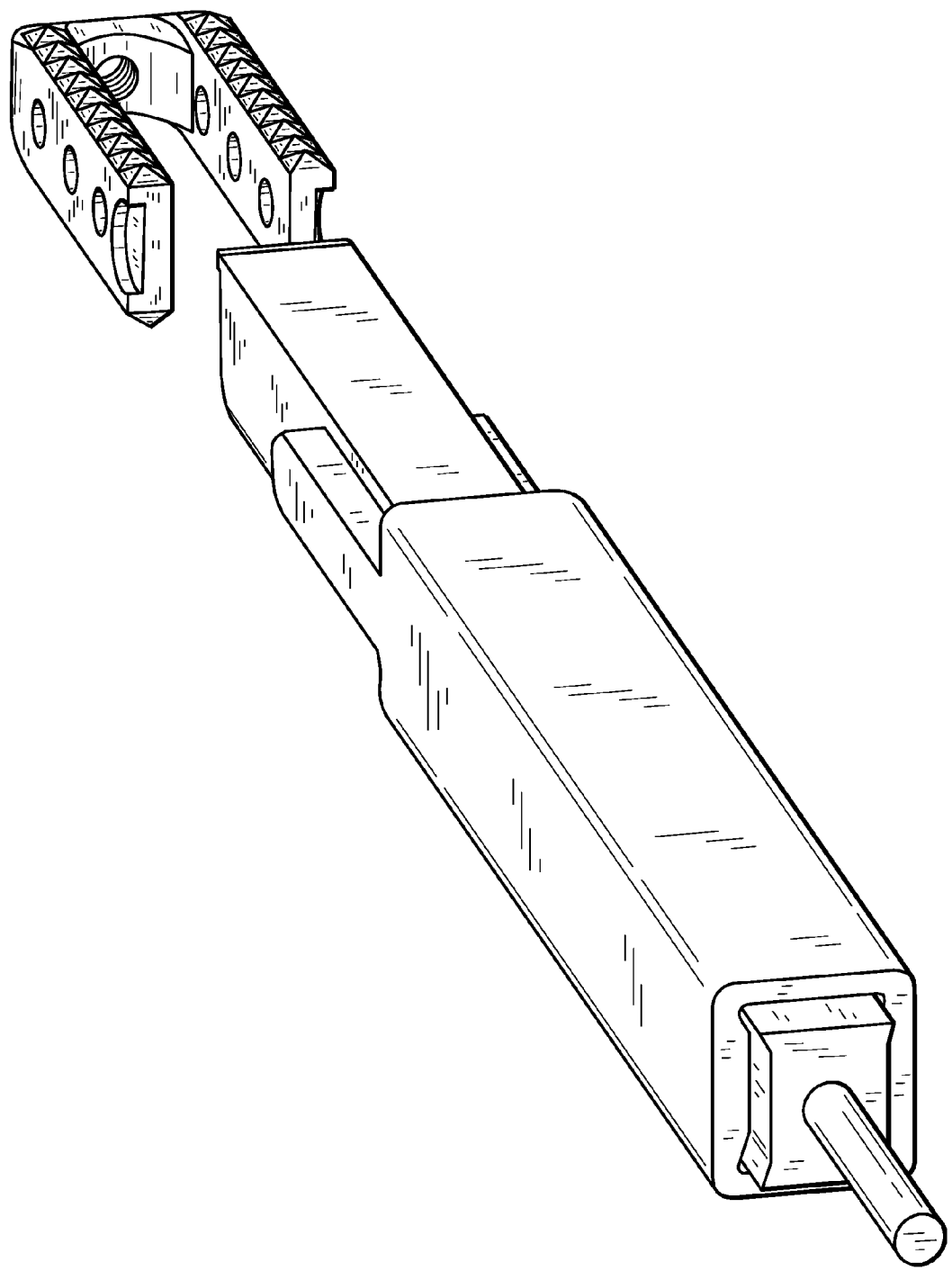
Figure 5D:
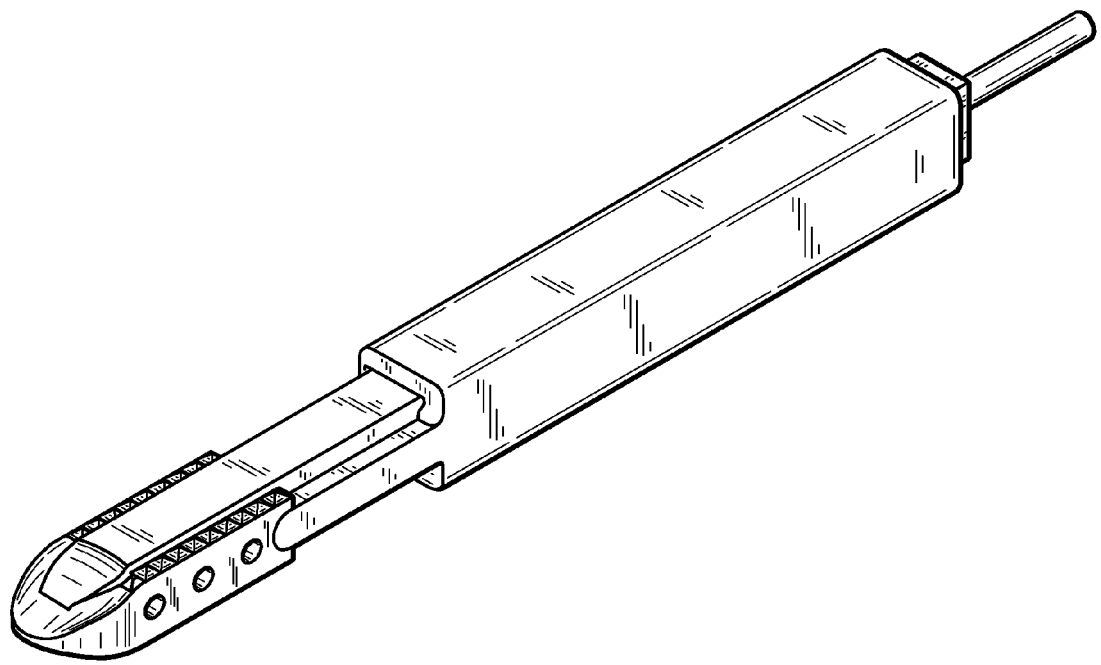
FIG. 5D is an assembled perspective view of the third cage-inserter assembly of the present invention.

FIGS. 5B and 5C are exploded versions of the cage and inserter assembly, as viewed from the distal and proximal and distal perspectives. The cage is the cage of FIG. 5A. The inserter assembly is substantially similar to that of FIGS. 4B and 4C, except that the arms 161 of the inner rod 163 are substantially shorter. The short arm and lack of cross-member allow the inner rod to bear substantially against the back surface 165 of the leading end 167 of the cage, thereby providing enhanced strength to the assembled design during insertion.

The assembled version of FIGS. 5B and 5C is shown in 5D. The assembled version is used in a manner substantially similar to that of the assembled version shown in 4D.

In some embodiments, hinges are provided between each end of the leading portion of the cage and each of the support members. These hinges allow the cage to be spread after insertion in order to increase the effective surface area (i.e., footprint) covered by the implant. Increasing the footprint beneficially improves the stability of the construct.

Now referring to FIGS. 6A-6D, there is provided an intervertebral fusion cage, comprising:
a) a C-shaped leading portion 201 having a first 203 and second 205 ends extending backwards, a front surface 207 and a back surface 209, the back surface having a recess 211 therein adapted for reception of a rod, an upper surface 213 and a lower surface 215, each of the upper and lower surfaces having a groove 217 extending from the front surface to the back surface for reception of a rail 255, 257, and a pivot hole 221 provided in each of the first and second ends that extends from the upper surface to the lower surface,
b) first 223 and second 225 support members extending proximally from the first and second ends of the C-shaped leading end, each support member having:
   i. an upper 227 and lower 229 surface adapted for bearing against and gripping adjacent vertebral bodies,
   ii. a back surface 231, the back surfaces forming an open trailing end therebetween,
   iii. a front end 235 having a pivot hole 237 which extends from the upper surface to the lower surface,
c) first 239 and second 241 pivot pins respectfully provided in the pivot holes to pivotally connect each end of the C-shaped leading end and the front end of each support member.

Therefore, in accordance with the present invention, there is provided an intervertebral fusion cage, comprising:
a) a leading portion having a first and second ends extending backwards, a front surface and a back surface, an upper surface and a lower surface, and a pivot hole provided in each of the ends which extends from the upper surface to the lower surface,
b) first and second support members, each support member having:
   i. an upper and lower surface adapted for bearing against and gripping adjacent vertebral bodies,
   ii. a back surface, the back surfaces forming an open trailing end therebetween,
   iii. a front end having a pivot hole which extends from the upper surface of the support member to the lower surface of the support member, and
c) first and second pivot pins respectfully provided in the pivot holes to pivotally connect each end of the leading end and the front end of each support member.

Each support member has a bump 245 extending medially from its inside surface 247. As will be explained later in more detail, these bumps facilitate the splaying of the support members to increase the footprint of the cage.

The insertion instrument of the present invention comprises three components;
a) a centrally-disposed cylindrical rod 251,
b) a pair of laterally disposed cage holders 253, and
c) upper 255 and lower 257 rails.

The cylindrical rod is adapted to fit within the open recess formed between the two support members. The rod comprises an enlarged head 259 having an annular recess 261 therebehind, a distal threaded portion 263 and an intermediate portion 265. The annular recess corresponds in shape and dimension to the bumps 245 situated on the inside surfaces of the support members. The distal threaded portion is adapted to be threadably received in the recess of the C-shaped leading portion of the cage, thereby securing the instrument to the cage. The intermediate portion of the rod is housed within the interior space of the cage.

In use, after cage insertion, the threaded portion is unthreaded to free the rod for proximal movement in respect of the cage. When the head of the cylindrical rod is moved backward so as to be removed from the cage, the hinged support members are forced to pivot outwards to increase the footprint of the cage. The closer these bumps are situated to the arcuate leading end of the cage, the greater the splay of the support members. The cylindrical rod is the first instrument component to be removed from the disc space.

The front ends 267 of the upper 255 and lower 257 rails are adapted to fit within the upper and lower grooves provided on the C-shaped leading portion of the cage, while the posterior portion of the rail is adapted to bear against the upper and lower surfaces of the cylindrical rod. Each rail has a thickness T that allows the rail to extend beyond the respective upper and lower surfaces of both the C-shaped leading portion and the support members of the cage. Further, the outer surfaces 271 of the rails are smooth. Because the smooth rails extend beyond the upper and lower surfaces of the cage, they provide a smooth insertion of the cage-instrument assembly into the disc space. For additional ease of insertion, the front end of each rail may be provided with a taper 272 that essentially extends from the taper of the front nose of the C-shaped leading portion of the cage. The rails are the second instrument component to be removed from the disc space.

Therefore, in accordance with the present invention, there is provided an intervertebral fusion cage comprising,
a) a leading end and a trailing end,
b) first and second longitudinal support members extending between each end, each member having an upper and lower surface adapted for bearing against and gripping adjacent vertebral bodies, each upper and lower surface having a longitudinal groove therein, and
c) a plurality of rails, each rail having a smooth outer surface and each rail received in a respective groove of the support member and extending out of the respective groove.

The pair of laterally disposed cage holders are disposed upon each side of the cylindrical rod. Each cage holder has a front end 273 adapted to bear against the back surface of each support member portion of the cage. These front ends prevent the cage from moving back when the cylindrical rod and the rails are removed. The cage holders are the third and last instrument component to be removed from the disc space.

Figure 6A:
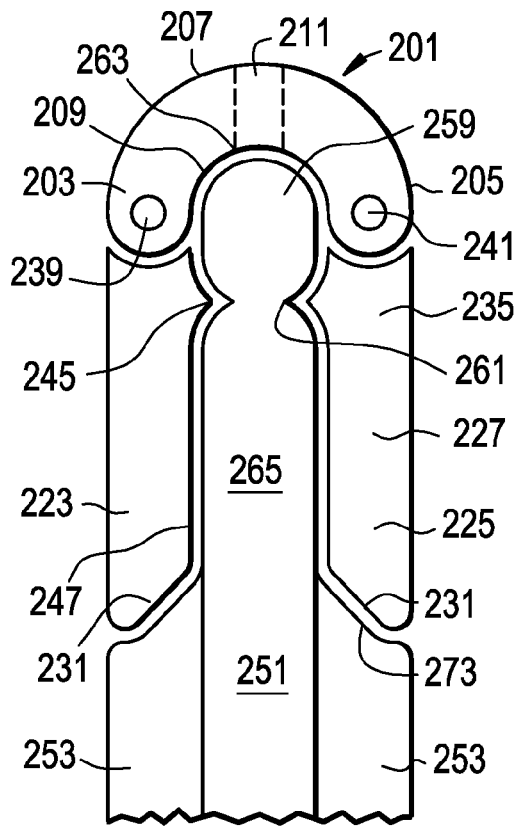
FIGS. 6A-6C are various views of a fourth cage-inserter assembly of the present invention.
Figure 6B:
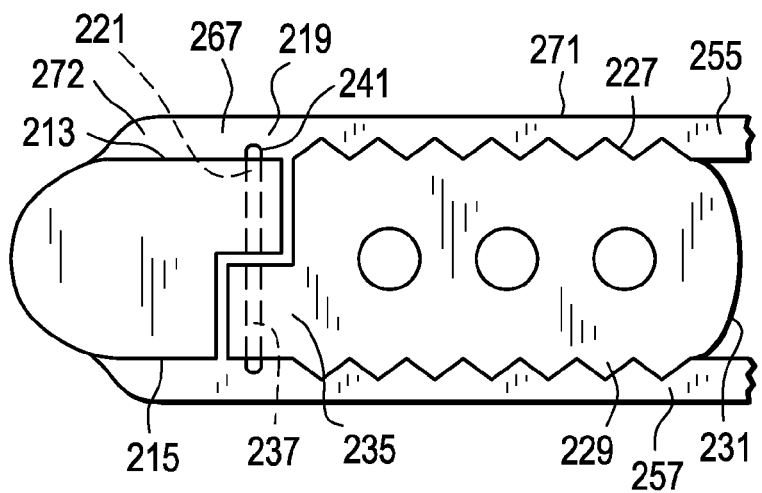
Figure 6C:
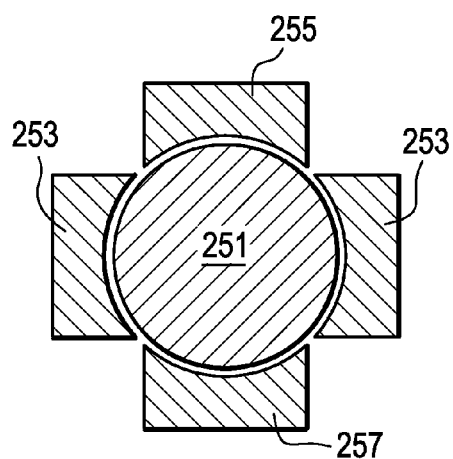
Figure 6D:
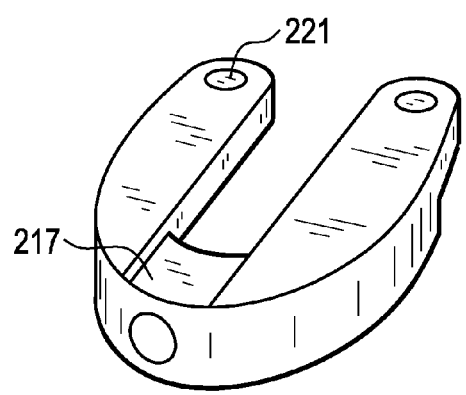
FIG. 6D is a perspective view of a leading end component of the present invention.
Figure 6E:
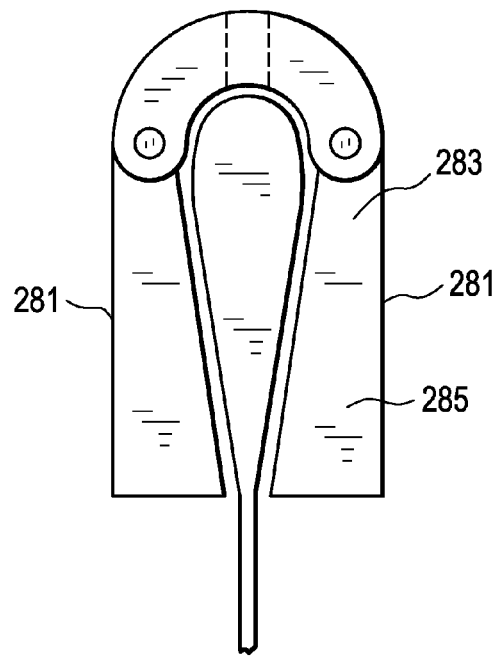
FIG. 6E is a plan view of a fifth cage-inserter assembly of the present invention.

Now referring to FIG. 6E, there is provided an intervertebral fusion cage, comprising:
a) a leading end having a right and left ends, a front surface and a back surface, the back surface being adapted for reception of a rod,
b) first and second support members 281, each member having a distal end 283 and widened proximal end 285, and an upper and lower surface adapted for bearing against and gripping adjacent vertebral bodies,
c) an open trailing end formed between the proximal ends, and
d) first and second hinges respectfully provided between each end of the leading end and the distal end of each support member.

As seen in FIG. 6E, each support member has a triangular cross-section. This configuration allows the proximal ends of the support members to extend inward to produce a narrowing at the proximal end. In addition, the inserter that fits within the inner space of the cage has a corresponding triangular shape. Thus, upon retraction of the inserter from the cage, the greater width of the distal end of the inserter pushes the proximal ends of the support members outward, thereby expanding the cross-section of the cage. The enlarged footprint of this expanded design beneficially provides stabilization of the construct. It also beneficially moves the struts towards the more dense bone on the periphery of the endplates.

Figure 7A:
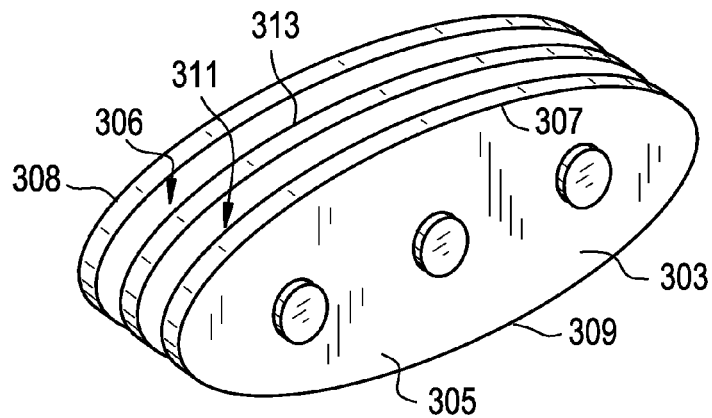
FIGS. 7A-7C are various views of a planked cage of the present invention.
Figure 7B:
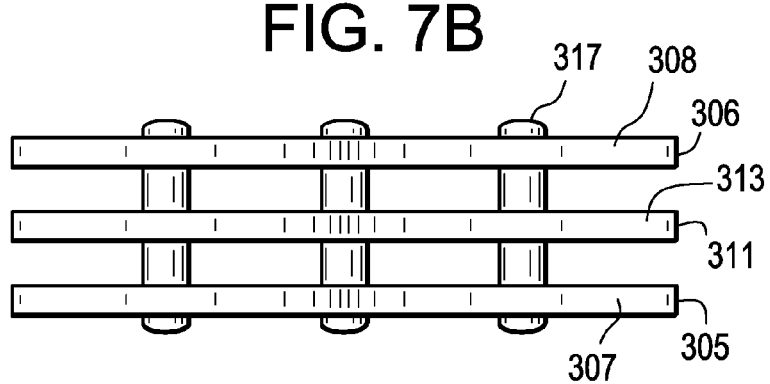

Now referring to FIGS. 7A-7B, there is provided an implant 301 for promoting bone fusion between adjacent vertebral bodies, said implant having an exterior surface 303, a longitudinal axis and comprising an assembly of components, the components comprising:
a) a first strut 305 having a first bone-engaging portion 307, an opposite second bone-engaging portion 309,
b) a second strut 311 spaced from said first strut, said second strut having a third bone-engaging portion 313, an opposite fourth bone-engaging portion, said second strut in cooperation with said first strut defining an internal space,
wherein the first strut and the second strut each include an aperture opening into the internal space;
c) an elongate cross-member 317 extending from the first strut to the second strut and including a first end engaged within the first aperture of the first strut and a second end engaged within the aperture of the second strut;
wherein the elongate cross-member is made of a metal.

As shown, FIGS. 7A and 7B also have d) a third strut 306 spaced from said first strut, said second strut having a third bone-engaging portion 308, an opposite fourth bone-engaging portion, said second strut in cooperation with said first strut defining an internal space.

Figure 7C:
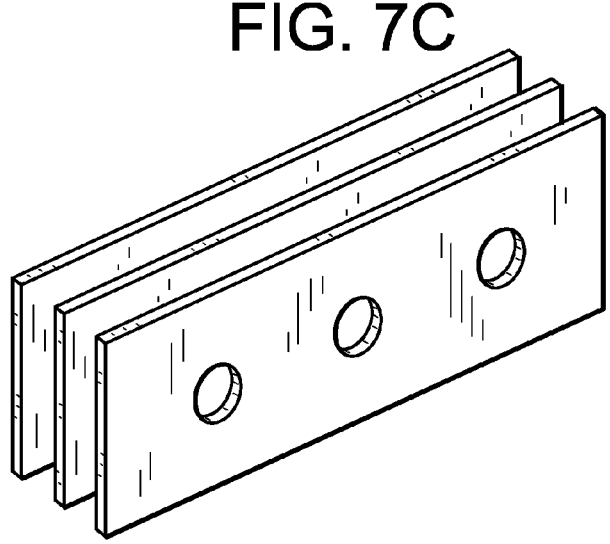

FIG. 7C provides a cage having substantial similarity to the cage of FIGS. 7A and 7B, except that it has a rectangular profile.

In preferred embodiments, the cage of FIG. 7C is constructed from parallel spaced planks made of woven carbon-fiber PEEK laminates spaced apart and held together by titanium pins (or "struts"). The spaces between the planks allow a metal instrument to mate with and attach to the pin component of the implant.

Figure 7D:
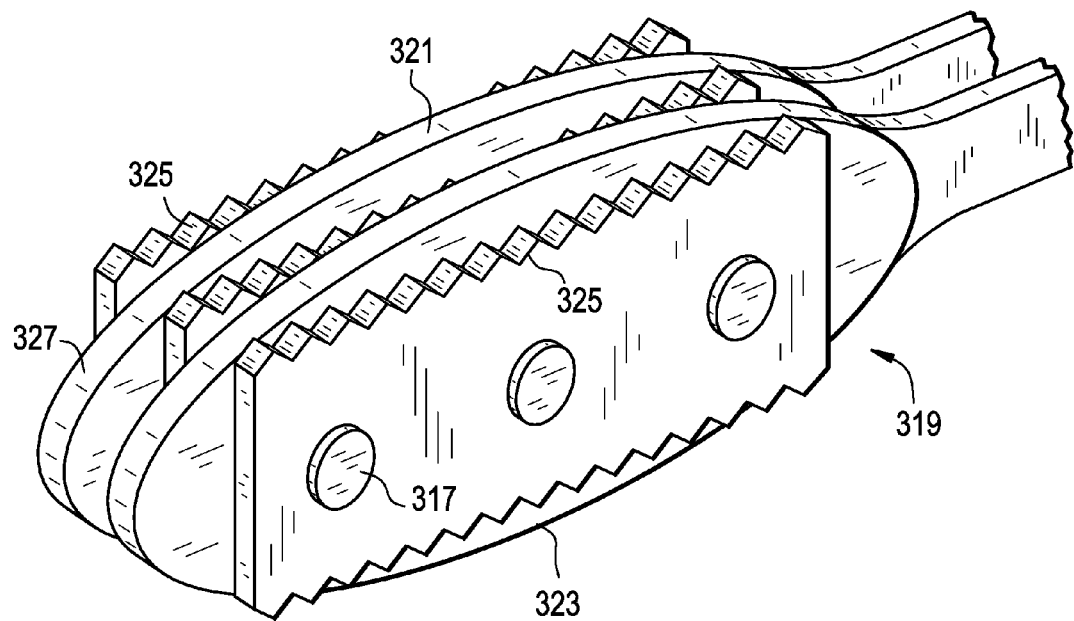
FIG. 7D is a perspective view of a planked cage-inserter assembly of the present invention.

Now referring to FIG. 7D, the metallic insertion instrument (or "inserter") 319 mates to the pins between the PEEK planks to form an assembly that can be easily inserted into and manipulated within the disc space. The inserter has smooth upper 321 and lower 323 surfaces that extend beyond the teeth 325 of the implant to provide for an easy insertion. The inserter also has a bulleted nose 327 to provide distraction. The implant is inserted into the disc space in an orientation that allows the planks to be substantially perpendicular to the patient's vertebral endplates.

The composite nature of this implant in conjunction with the mating condition of the inserter instrument will also allow for very forceful manipulation of the implant during insertion without damaging the implant. In essence, the PEEK laminates are not loaded by the insertion force.

Since the pins 317 are mainly in compression between the inserter components, the inserter will carry the majority of the insertion load. To the extent the pins 317 carry any impaction force, the pins are advantageously made of a high strength, ductile metal such as titanium, and are preferably a titanium alloy, and so can bear such loads. The metallic nature of the pins allows for forceful manipulation of the assembly during insertion into the disc space. At the same time, selection of a somewhat flexible polymer such as PEEK for the material of construction of the laminate components avoids the stress shielding issues associated with purely titanium cage designs. Selection of the woven carbon fiber (as opposed to chopped carbon fiber) will enhance the strength of the PEEK composite.

FIG. 7C shows a cage made of three parallel planks held together by three titanium-based pins. However, in other embodiments, only two planks may be used to construct the cage. Likewise, more than three planks may also be used to construct the cage.

In some embodiments, as in FIG. 7A, the struts 305, 311 can have domed upper and lower surfaces in order to conform to the shape of the vertebral endplates. However, in other embodiments, the upper and lower surfaces of the struts are flat (as in FIG. 7C) and the inserter instrument is provided with a bullet nose 327 that extends distal of the implant (as in FIG. 7D).

In some embodiments, the struts have additional side holes (not shown), wherein those side holes are not engaged by a cross-pin. The presence of these holes will enhance bone ingrowth through the struts.

In some embodiments, the upper and lower surfaces of the struts have a plurality of fine teeth 325 extending therefrom to resist implant migration.

Figure 8A:
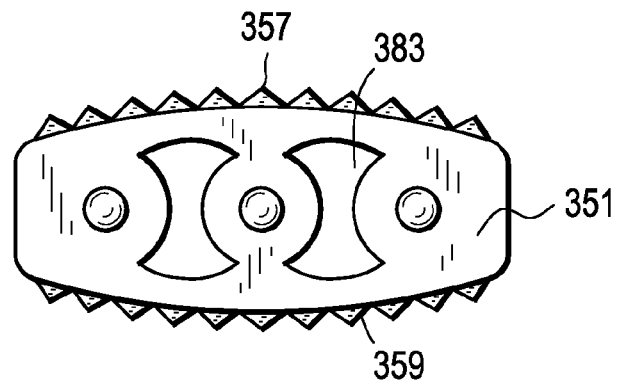
FIGS. 8A and 8B are views of a planked cage of the present invention.
Figure 8B:
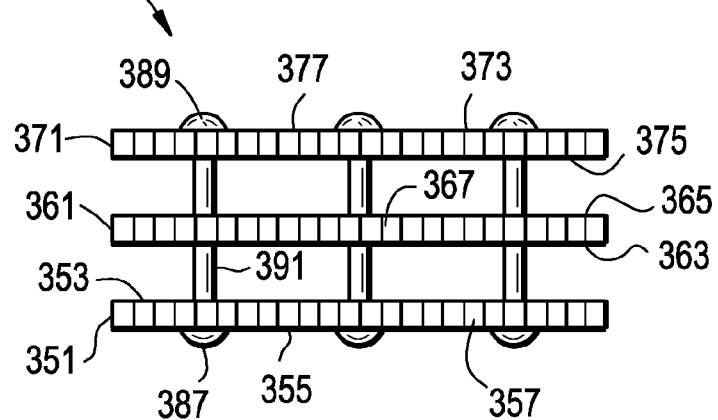
Figure 8C:
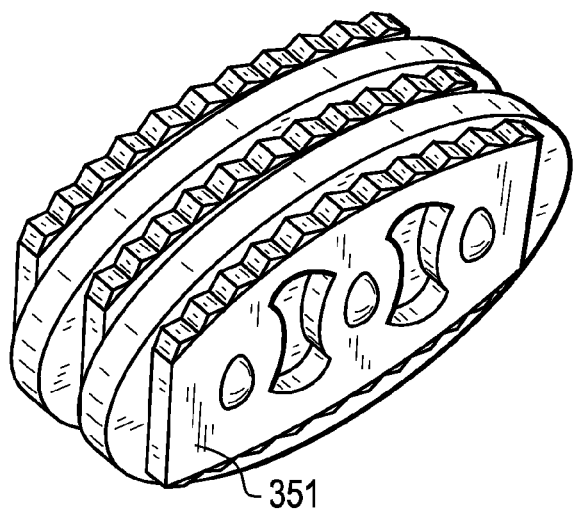
FIG. 8C is a perspective view of a planked cage-inserter assembly of the present invention.

Now referring to FIGS. 8A-8C, there is provided an intervertebral fusion cage, comprising:
a) a first strut 351 having first 353 and second 355 sides, an upper bone-engaging portion 357, and a lower bone-engaging portion 359,
b) a second strut 361 having first 363 and second 365 sides, said second strut having an upper bone-engaging portion 367, a lower bone-engaging portion, the first side of the second strut opposed to the first side of the first strut thereby defining a first internal space,
c) a third strut 371 having first 373 and second 375 sides, said third strut having an upper bone-engaging portion 377, a lower bone-engaging portion, the second side of the second strut opposed to the second side of the third strut thereby defining a second internal space,
wherein the first strut, second strut and third strut each include a plurality of apertures extending between the respective first and second sides thereof;
wherein the first strut, second strut and third strut each include a first opening 383 adapted for bone growth extending between the respective first and second sides thereof;
d) a first elongate cross-member 385 extending from the first strut to the third strut and including a first end 387 engaged within a first aperture of the first strut and a second end 389 engaged within a first aperture of the third strut, and an intermediate portion 391 engaged within a first aperture of the second strut In some embodiments, the fusion cage includes smooth retractable rails positioned on the top and bottom of the cage. Now referring to FIGS. 9A and 9B, there is provided an intervertebral fusion cage comprising:
a) a leading end 401 and a trailing end 403,
b) first 405 and second 407 longitudinal support members extending between each end, each member having an upper 409 and a lower 411 surface adapted for bearing against and gripping adjacent vertebral bodies, each upper and lower surface having a longitudinal groove 413 therein, and
c) a rail 415 having a smooth outer surface 416 and received in a respective groove and extending out of the respective groove.

Figure 9A:
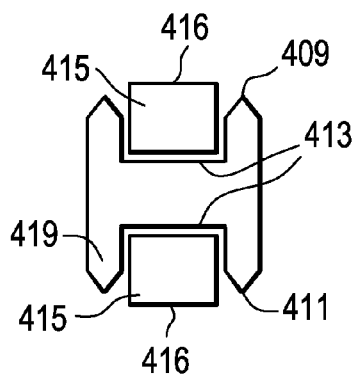
FIG. 9A is a cross section of a banana cage-inserter assembly of the present invention.
Figure 9B:
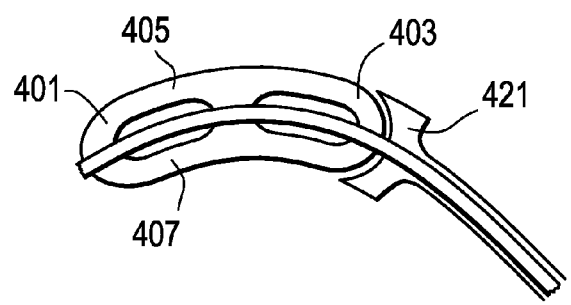
FIG. 9B is a top view of a banana cage-inserter assembly of the present invention.

As shown in FIG. 9A, the upper and lower surface of the cage has teeth 419 that extend outward to grip the adjacent vertebral bodies. The rails also extend past the respective teeth of each of the upper and lower surfaces. During insertion of this cage, the smooth rails are the only part of the cage that contacts the adjacent vertebral bodies, and so only a moderate insertion force is required to insert the cage into the disc space. Now referring to FIG. 9B, once the cage is set in place, the rails are proximally retracted by the surgeon (while the back end of the cage is still held by the inserter 421), the adjacent boney endplates of the patient collapse upon the cage, and the aggressive teeth of the cage will engage the bone and effectively prevent migration of the implant. Therefore, the cage and inserter of the present invention overcome the prior art problems associated with conventional toothed and smooth cages by not only allowing for easy insertion but also providing a firm, migration-resistant grip.

In some embodiments, the rails are rigid. Such rigid rails may be conveniently used with substantially straight cages. In some embodiments, the rails are flexible. Such flexible rails may be conveniently used with curved cages such as banana cages.

In some embodiments (not shown), the rail comprises an outer tube having a smooth outer surface and an inner rod. When assembled, the tube and rod have a height that allows the to extend outward past the upper and lower teeth of the cage. During insertion, the tube-rod assembly eases insertion load. When the cage has been inserted, the rod is withdrawn and the tube collapses under the force of the tensioning load of the functional spinal unit. Thus, the adjacent boney endplates of the patient collapse upon the cage, and the aggressive teeth of the cage will engage the bone and effectively prevent migration of the implant.

In some embodiments (not shown), the rails can be molded onto the cage as a fast dissolving polymer. During insertion, the smooth rails ease insertion. Once the cage is set in place, the rails dissolve, thereby allowing the adjacent boney endplates of the patient to collapse upon the cage.

In some embodiments, a single smooth cable may act as both an upper and lower rail by wrapping around an end of the cage. During insertion, the smooth rails ease insertion. At this time, tensioning of the cable may serve to hold the cage on the inserter.

Once the cage is set in place, the surgeon pulls a single end of the cable in order to remove the whole cable from the cage. In some embodiments, the cable is coated with a smoothing polymer such as Teflon in order to reduce friction.

The recognition that inserter designs can now occupy the interior volume of the cage has special application in the field of intervertebral fusion cages having a banana shape. In these banana cages, the cage can be made to attach to an inserter at the midpoint of the cage, which is the strongest portion of the cage.

Figure 10A:
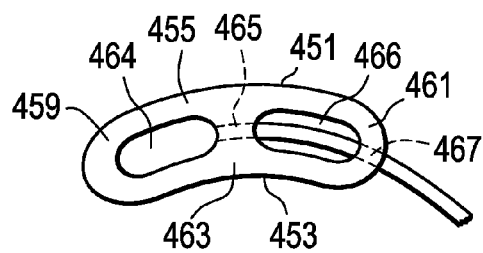
FIGS. 10A-10B are top views of banana cage-inserter assemblies of the present invention.

Now referring to FIG. 10A, there is provided an intervertebral fusion cage having:
a) a convex anterior surface 451 and a concave posterior surface 453,
b) an upper bone engaging surface 455 and a lower bone engaging surface (not shown),
c) leading 459 and trailing 461 side surfaces,
d) a strut 463 connecting the convex anterior surface and the concave posterior surface and thereby forming leading 464 and trailing 466 spaces,
wherein the strut has a threaded recess opening 465 onto the trailing space for reception of a threaded distal end of an inserter and,
wherein the trailing side surface has a throughhole 467 therethrough for slidable reception of the inserter.

Figure 10B:
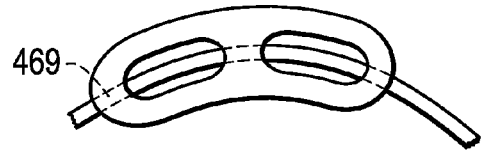

Now referring to FIG. 10B, there is provided an intervertebral fusion cage having substantial similarity to that of FIG. 10A, except that its leading side surface also has a throughhole 469 adapted for slidable reception of a rail.

Typically, the inserter of the present invention can be made out of any material commonly used in medical instruments. If the inserter is designed to be reusable, then it is preferred that all of its components be made of stainless steel. If the device is designed to be disposable, then it is preferred that at least some of the components be made of plastic. Preferably, at least one component of the inserter is sterilized. More preferably, each component is sterilized.

The intervertebral fusion cage of the present invention may be manufactured from any biocompatible material commonly used in interbody fusion procedures. In some embodiments, the cage is made from a composite comprising 40-99% polyarylethyl ketone PAEK, and 1-60% carbon fiber. Such a cage is radiolucent. Preferably, the polyarylethyl ketone PAEK is selected from the group consisting of polyetherether ketone PEEK, polyether ketone ketone PEKK, polyether ketone ether ketone ketone PEKEKK, and polyether ketone PEK. Preferably, cage is made from woven, long carbon fiber laminates. Preferably, the PAEK and carbon fiber are homogeneously mixed. Preferably, the composite consists essentially of PAEK and carbon fiber. Preferably, the composite comprises 60-80 wt % PAEK and 20-40 wt % carbon fiber, more preferably 65-75 wt % PAEK and 25-35 wt % carbon fiber. In some embodiments, the cage is made from materials used in carbon fibers cages marketed by DePuy Spine, Raynham, Mass., USA. In some embodiments, the composite is PEEK-OPTIMA™, available from Invibio of Greenville, N.C.

In other embodiments, the cage is made from a metal such as titanium alloy, such as Ti-6Al-4. In other embodiments, the cage is made from an allograft material. In some embodiments, the cage is made from ceramic, preferably a ceramic that can be at least partially resorbed, such as HA or TCP. In other embodiments, the ceramic comprises an oxide such as either alumina or zirconia. In some embodiments, the cage is made from a polymer, preferably a polymer that can be at least partially resorbed, such as PLA or PLG.

In preferred embodiments, the cage is provided in a sterile form.

In summary, the cage implant of the present invention distracts the disc space during insertion. It is easy to insert and optimizes clinical performance once in place because it resists migration and subsidence, has an appropriate stiffness for load sharing, is preferably radiolucent and has a shape that is able to contain injected graft material such as growth factors. In addition, the cage is robust over a wide variation of surgical technique because it will not break even when large forces are applied thereto.

The cage of the present invention is compatible with the broad use of injectable paste-like bone grafting materials, such as BMP-containing pastes because it is designed to be inserted empty and then filled with graft in—situ. With the availability of these injectable pastes, cages will no longer require large, contiguous internal volumes to accept morselized/granular bone graft. Spaces can be smaller and more numerous.

The cage of the present invention allows an insertion instrument to occupy the internal volume of the cage so as to minimize the overall size of the inserted cage as well as to bear insertion loads. The inserter can also possess smooth upper and lower surfaces to reduce friction and thereby increase the ease of insertion. The cage of the present invention will not experience large loads during insertion.

I claim:
1. An intervertebral fusion cage comprising:
a) a leading portion having first and second ends, a front surface having a tapered insertion nose and a back surface opposite the front surface, the back surface having a recess therein adapted for reception of a rod, an upper surface and a lower surface opposite the upper surface, wherein the leading portion defines a first pivot hole at the first end, the leading portion defines a second pivot hole at the second end, and each of the first and second pivot holes extend from the upper surface to the lower surface;

b) first and second support members extending from the first and second ends, respectively, each support member having 1) an upper surface and a lower surface configured to bear against and grip adjacent vertebral bodies, and 2) a front end having a pivot hole that extends from the upper surface to the lower surface;

c) a first pivot pin disposed in both the first pivot hole of the leading portion and the pivot hole of the front end of the first support member, thereby pivotally connecting the first support member to the leading portion; and d) a second pivot pin disposed in both the second pivot hole of the leading portion and the pivot hole of the front end of the second support member, thereby pivotally connecting the second support member to the leading portion, wherein the first and second support members are configured to pivot outwards about the respective first and second pivot pins to increase a footprint of the cage.

2. The intervertebral fusion cage as recited in claim 1, wherein the first and second ends of the leading portion are spaced from each other along a first direction, and the front surface of the leading portion at the tapered nose is curved as it extends along the first direction.

3. The intervertebral fusion cage as recited in claim 2, wherein the lower surface of the leading portion is opposite the upper surface of the leading portion along a second direction that is perpendicular to the first direction, and the nose is tapered along a plane that is defined by the first direction and a third direction that is perpendicular to each of the first and second directions.

4. The intervertebral fusion cage as recited in claim 1, wherein the first and second support members define a space therebetween, the space sized to receive the rod when the rod extends into the recess.

5. The intervertebral fusion cage as recited in claim 4, wherein the recess is threaded.

6. The intervertebral fusion cage as recited in claim 1, wherein the footprint is defined along a plane that is normal to a direction of elongation of each of the first and second pivot pins.

7. The intervertebral fusion cage as recited in claim 1, wherein the first and second support members are spaced from each other along a first direction, the upper and lower surfaces of each of the first and second support members are spaced from each other along a second direction perpendicular to the first direction, and the footprint is defined along a plane that includes the first direction and a third direction that is perpendicular to each of the first and second directions.

8. The intervertebral fusion cage as recited in claim 7, wherein the first support member extends from the leading portion to a first back surface of the first support member, the second support member extends from the leading portion to a second back surface of the second support member, and movement of the leading portion along the third direction relative to both the first and second back surfaces causes the first and second support members to pivot outwards about the respective first and second pivot pins.

9. The intervertebral fusion cage as recited in claim 1, wherein the first and second members define a first position prior to outwardly pivoting about the respective first and second pivot pins, the first and second members define an expanded position after they have pivoted about the respective first and second pivot pins, and the first and second members are oriented parallel to each other when they are in the first position.

10. The intervertebral fusion cage as recited in claim 1, wherein each of the first and second support arms comprise teeth at their respective upper and lower surfaces.

11. An intervertebral fusion system comprising:
an intervertebral fusion cage that is expandable from a first position to an expanded position, the intervertebral fusion cage including:
a leading portion;
a first support member that extends from the leading portion in a first direction when the intervertebral fusion cage is in the first position, and a first pivot pin that extends into both the leading portion and the first support member so as to pivotally connect the first support member to the leading portion; and
a second support member that extends from the leading portion in the first direction when the intervertebral fusion cage is in the first position, and a second pivot pin that extends into both the leading portion and the second support member so as to pivotally connect the second support member to the leading portion; and
a rod capable of being disposed between the first and second support members, such that when the intervertebral fusion cage is in the first position, a portion of the rod is straddled by the first and second support members,
wherein when the rod is disposed between the first and second support members and the intervertebral fusion cage is in the first position, movement of the rod in the first direction causes the intervertebral fusion cage to move from the first position to the expanded position, whereby the first and second support members pivot away from each other about the first and second pivot pins, respectively, such that the first and second support members flare away from each other as they extend away from the leading portion.

12. The intervertebral fusion system as recited in claim 11, wherein the rod is configured to be oriented in the first direction as it is moved in the first direction so as to cause the intervertebral fusion cage to move from the first position to the expanded position.

13. The intervertebral fusion system as recited in claim 11, wherein the rod is removably attachable to the leading portion at a location between the first and second pivot pins.

14. The intervertebral fusion system as recited in claim 13, wherein the rod is removably received in a recess of the leading portion when the intervertebral fusion cage is in the first position and the portion of the rod is straddled by the first and second support members.

15. The intervertebral fusion system as recited in claim 14, wherein the rod is threadedly received in the recess.

16. The intervertebral fusion system as recited in claim 11, wherein,
each of the leading portion, the first support arm, and the second support arm defines a respective upper surface and a lower surface that are configured to bear against respective adjacent vertebral bodies,
the leading portion defines first and second pivot holes that extend from the upper surface of the leading portion to the lower surface of the leading portion,
the first support arm defines a pivot hole that extends from the upper surface of the first support arm to the lower surface of the first support arm, the second support arm defines a pivot hole that extends from the upper surface of the second support arm to the lower surface of the second support arm, the first pivot pin is disposed in both the first pivot hole and the pivot hole of the first support arm, and the second pivot pin is disposed in both the second pivot hole and the pivot hole of the second support arm.

17. The intervertebral fusion system as recited in claim 16, wherein the first and second arms are spaced from each other along a second direction that is perpendicular to the first direction, the upper and lower surfaces are spaced from each other along a third direction that is perpendicular to both the first direction and the second direction, and the first and second pivot pins are oriented along the third direction.

18. The intervertebral fusion system as recited in claim 11, wherein the support arms are parallel to each other when the intervertebral fusion is in the first position.

19. An intervertebral fusion system comprising:
a) an intervertebral fusion cage that is expandable from a first position to an expanded position, the intervertebral fusion cage including:
  i. a leading portion;
  ii. a first support member that extends from the leading portion, and a first pivot pin that extends into both the leading portion and the first support member so as to pivotally connect the first support member to the leading portion; and
  iii. a second support member that extends from the leading portion, and a second pivot pin that extends into both the leading portion and the second support member so as to pivotally connect the second support member to the leading portion; and
b) an insertion instrument including:
  i. an instrument component that is capable of bearing against the intervertebral fusion cage; and
  ii. a rod that extends out from the instrument component, wherein when the intervertebral fusion cage is in the first position and the rod is disposed between the first and second support members, movement of the rod relative to the instrument component, while the instrument component bears against the intervertebral fusion cage, causes the intervertebral fusion cage to move to the expanded position, whereby the first and second support members pivot away from each other about the first and second pivot pins, respectively.

20. The intervertebral fusion system as recited in claim 19, wherein,
the first support member extends from the leading portion to a first back surface of the first support member in a proximal direction when the intervertebral fusion cage is in the first position, the second support member extends from the leading portion to a second back surface of the second support member in the proximal direction when the intervertebral fusion cage is in the first position, and movement of the rod relative to the instrument component in the proximal direction, while the instrument component bears against the intervertebral fusion cage, causes the intervertebral fusion cage to move from the first position to the expanded position.

21. The intervertebral fusion system as recited in claim 20, wherein the first and second arms straddle a portion of the rod when the intervertebral fusion cage is in the first position.

22. The intervertebral fusion system as recited in claim 21, wherein the leading portion has first and second ends, a front surface having a tapered insertion nose and a back surface, and an upper surface and a lower surface each configured to bear against adjacent vertebral bodies.

23. The intervertebral fusion system as recited in claim 19, wherein the rod extends out from the instrument component in a distal direction, and movement of the rod relative to the instrument component in a proximal direction, opposite the distal direction, while the instrument component bears against the intervertebral fusion cage, causes the intervertebral fusion cage to move from the first position to the expanded position.

* * * * *